United States Patent [19]

Suzuki et al.

[11] 4,019,957

[45] Apr. 26, 1977

[54] PROCESS FOR PRODUCING (2'-AMINO-2'-DEOXYPENTOFURANOSYL) GUANINE

[75] Inventors: Takeo Suzuki, Hofu; Toshihide Nakanishi, Machida, both of Japan

[73] Assignee: Kyowa Hakko Kogyo Kabushiki Kaisha, Tokyo, Japan

[22] Filed: July 19, 1976

[21] Appl. No.: 706,865

Related U.S. Application Data

[62] Division of Ser. No. 516,708, Oct. 21, 1974, Pat. No. 3,987,030.

[52] U.S. Cl. .............................................. 195/28 N
[51] Int. Cl.² ........................................ C12D 13/06

[58] Field of Search ..................... 195/28 N, 29, 96

[56] References Cited

UNITED STATES PATENTS 3,763,008  10/1973  Nakayama ...................... 195/28 N

*Primary Examiner*—Lionel M. Shapiro
*Attorney, Agent, or Firm*—Wolder & Gross

[57] ABSTRACT

The present invention relates to the production of a new compound (2'-amino-2'-deoxypentofuranosyl) guanine by a fermantation process using a microorganism belonging to the genus Aerobacter.

8 Claims, 3 Drawing Figures

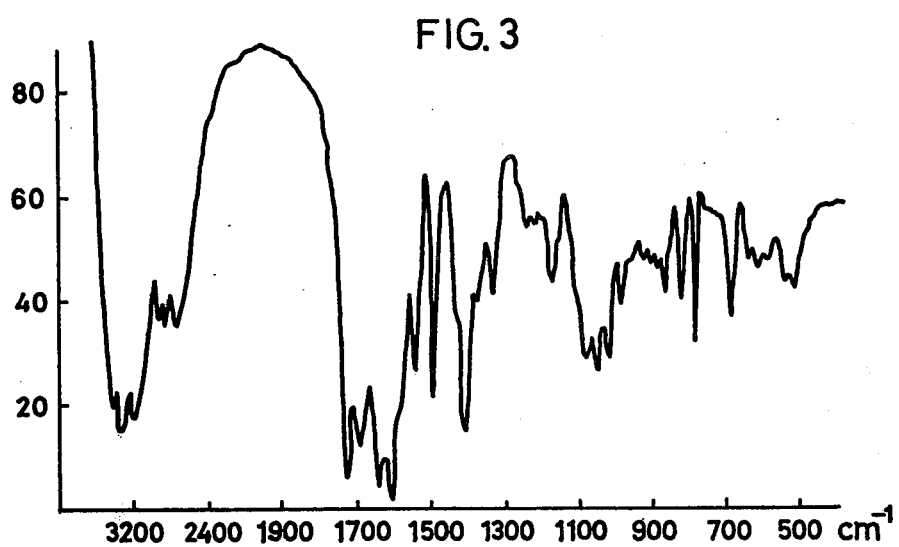

PROCESS FOR PRODUCING (2'-AMINO-2'-DEOXYPENTOFURANOSYL) GUANINE

This is a division of application Ser. No. 516,708, filed Oct. 21, 1974, now U.S. Pat. No. 3,987,030, issued Oct. 19, 1976.

BRIEF DESCRIPTION OF THE DRAWINGS

FIG. 3 shows the infra-red absorption spectrum of (2'-amino-2'-deoxypentofuranosyl) guanine

DESCRIPTION OF THE INVENTION

This invention relates to a new compound relating to nucleic acids. More particularly, this invention relates to a new guanosine analogue designated as (2'-amino-2'-deoxypentofuranosyl) guanine.

The present invention is based upon the discovery that microorganisms belonging to genus Aerobacter are capable of producing a new substance which exhibits similar characteristics to those of guanosine as determined by paper chromatography, UV absorption spectra and the like. After isolation and identification, it was confirmed that this substance was a new guanosine analogue which may be used in analogous manner to those of other guanosine analogues.

This invention also relates to a process for producing said new guanosine analogue by fermentation.

According to the present invention, a new compound represented by the following general formula is obtained:

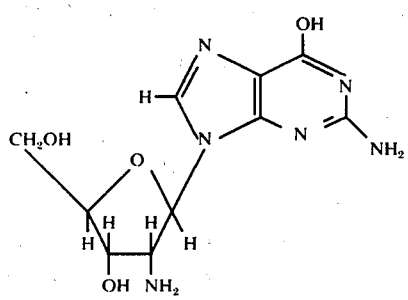

(2'-amino-2'-deoxypentofuranosyl) guanine (hereinafter designated as 2'-APG) which is the new guanosine analogue according to the present invention can easily be isolated in the form of white plate-like crystals having alkaline nature by concentrating, under reduced pressure, a solution of it in a suitable solvent such as, for example, water.

Figure 1:
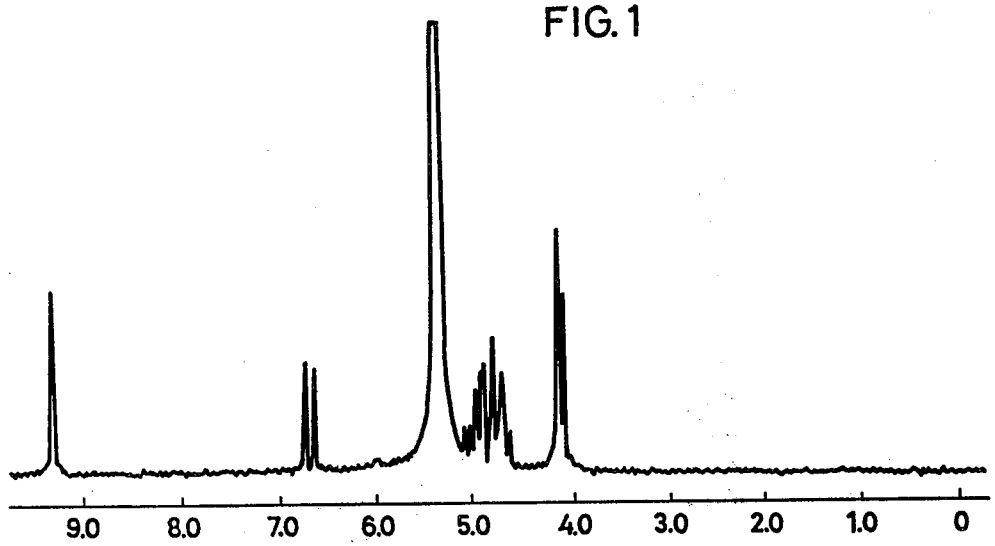
FIG. 1 shows the nuclear magnetic resonance spectrum of (2'-amino-2'-deoxypentofuranosyl) guanine.
Figure 2:
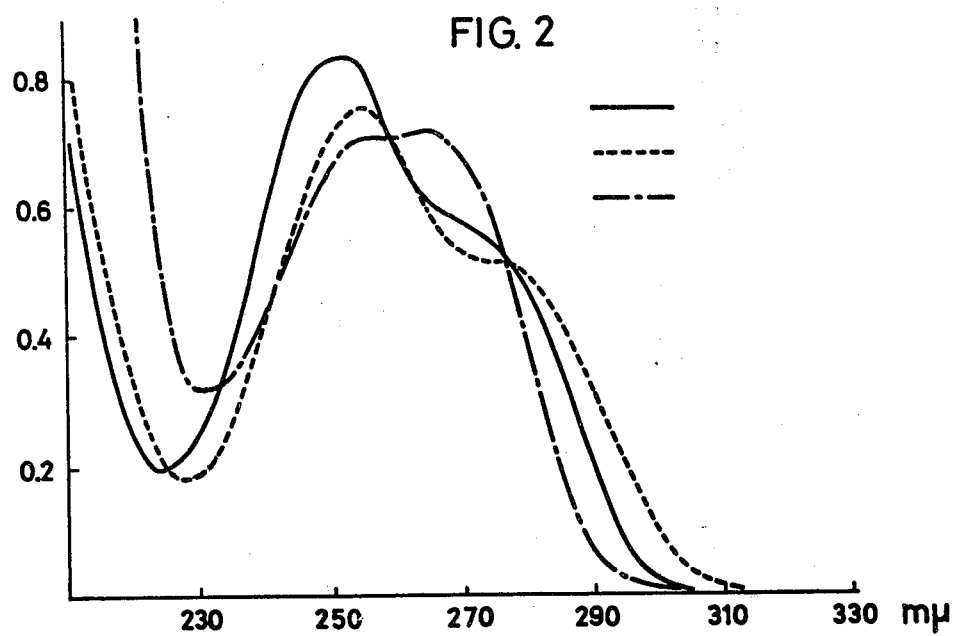
FIG. 2 shows the ultra-violet absorption spectra of (2'-amino-2'-deoxypentofuranosyl) guanine.

The new guanosine analogue exhibits the following maximum absorptions of UV spectra, as shown in FIG. 2.

| at (mμ) | in |
|---|---|
| 253 | neutral aqueous solution |
| 256 | 0.1N HCl solution |
| 258 & 266 | 0.1N NaOH solution |

Rf values of the new guanosine analogue when determined by paper chromatography using No. 50 Filter Paper (available from Toyo Roshi Kabushiki Kaisha, Japan) are as follows:

| RF value | When developed by |
|---|---|
| 0.22 | n-butanol:acetic acid:water (4:1:2) |
| 0.35 | isopropanol:HCl (65:16.7)with addition of water to give a total of 100 |
| 0.51 | ethanol: 1 N ammonium acetate (75:30) |

As to the color reaction, the orcinol test and diphenylamine tests are negative.

Elemental analysis, empirical formula and molecular weight of the new compound are as follows:

Elemental analysis
C : 42.60 H : 4.95 N : 29.81
Empirical formula $C_{10}H_{14}N_6O_4$
Molecular weight 282.26

When the new compound is hydrolysed with 1N HCl for one hour in a boiling water bath and then subject to paper chromatography, aminopentose is observed as follows:

| When developed by | position of Rf |
|---|---|
| n-butanol:pyridine:water (6:4:3) | at 0.28 |
| n-butanol:ethyl acetate: water (7:1:2) | 0.42 |
| n-butanol:acetic acid: water (4:1:2) | 0.31 |

This aminopentose is colored as follows, thereby confirming it as 2'-aminopentose.

| colour | by |
|---|---|
| pink | p-anisidine reagent |
| purple | ninhydrin reagent |
| pink | Elson-Morgan's procedure |
| blue | Tsuji-Kinoshita reaction |

In addition, results obtained by IR spectrum and nuclear magnetic resonance also serves to identify the new compound of the present invention.

The new compound of the present invention has excellent physiological activity and does not exhibit any toxity for example when administered to the abdominal cavity of DD-type mouse in an amount of 800 mg per Kg of mouse. Anti-cancer activity is observed when this new compound is administered intravenously in an amount of 120mg/Kg per day continuously for 8 days to a mouse which has been transplanted with Salcoma 180 solid-type cancer, 10 mcg/ml of this new compound inhibits the growth of cancer cells HeLa $S_3$ in vitro.

400 mg of crystalline 2'-APG is hydrolysed with 1N HCl at a temperature of 100° C for 1 hour, and passed through Dowex 50W ($H^+$ form, tradename for an ion exchange resin, available from Dowex Chemical Inc., USA). The sugar fraction of the 2'-APG is isolated as hydrochloride which is then crystallized with a methanolacetone solution to give 100 mg of crystalline product. The decomposition temperature of the crystalline product is 143°–150° C and its angle of optical rotation is $[\alpha]_D^{27} =_{30} 13°4$ (initial, extra-polated) → $-3.5°$ (C = 0.75, $H_2O$). By comparing the results obtained with the standard values of synthesized 2-aminopentose, it is found that the sugar part of the crystalline 2'-APG is D-2-amino-2-deoxyribose. 2'-

APG according to the present invention has an angle of optical rotation of $[\alpha]_D^{26} = -56.6°$ (C = 0.5, H$_2$O). On the other hand, the angle of optical rotation of the guanosine (9-β-ribofuranosyl guanine) is $[\alpha]_D^{26} = -72°$ (C = 1.4, O.1N NaOH). The angles of optical rotation of adenosines which are analogous compounds to 2'-APG of the present invention are as follows:

i. 9-β-adenosine
  $[\alpha]_D^{11} = -61.7°$ (C = 0.706, H$_2$O)
ii. 9-α-2'-amino-2'-deoxyadenosine
  $[\alpha]_D^{23} = +90° \pm 2°$ (C = 0.635, methanol)
iii. 9-β-2'-amino-2'-deoxyadenosine
  $[\alpha]_D^{22} = -66° \pm 2°$ (C = 0.98, methanol)

From the above results, it is confirmed that 2'-APG of the present invention has a β- conformation.

The present invention relates further to a process for producing a new guanosine analogue by fermentation.

Any and all micoorganisms which belong to the genus Aerobacter (Enterobacter) may be used for the process of the present invention. The species of microorganism which has been found especially useful for the process of the present invention is *Aerobacter cloacae* (*Enterobacter cloacae*) (FERM-P No. 1893).

The microorganisms referred to in the present specification are freely available to the public from the Fermantation Research Institute, Agency of Industrial and Technology, Japan.

Carbon sources which may be used for the culture medium used in the present invention include carbohydrates such as glucose, sucrose, starch, sorbitol etc., alcohols, and organic acids such as acetic acid, etc.

Suitable nitrogen sources include, for example, inorganic nitrogen compounds such as ammonium sulphate, etc. and organic nitrogen compounds such as meat extract, yeast extract, peptone, etc.

In carrying out the process of the present invention, the culture medium containing the above-mentioned carbon source, nitrogen source, inorganic compounds such as phosphate, sulphate, hydrochloride, metallic salt such as iron, mananese, magnesium, potassium, sodium, etc. and growth-promoting factors is sterilized and then inoculated with the aforesaid microorganism for aerobic culturing. It is possible to improve the yield of the new compound by adding purine nucleotides such as inosinic acid, xanthylic acid, guanylic acid, etc. or its precursor to the medium.

The cultivation may be effected at a temperature of from 20° to 40° C and a pH of from 5 to 8, preferably from 6 to 7. In this case, the pH is adjusted by the addition of urea solution, aqueous ammonia or ammonium carbonate. The cultivation is completed when the amount of 2'-APG produced reaches a maximum period of from 1 to 7 days is usually sufficient for effecting cultivation.

When isolating the 2'-APG produced, cell bodies are removed from the culture medium by means of centrifugation or filtration. The 2'-APG is then recovered from the culture liquor by passing the liquor through an acidic ion exchange resin to selectively absorb the 2'-APG thereon. If necessary, absorbing agents may be used. The 2'-APG is eluted using, for example, water or aqueous ammonia and the eluate is concentrated under reduced pressure to produce purified crystalline 2'-APG.

The following non-limitative examples further illustrate the present invention.

EXAMPLE 1

*Aerobacter cloacae* (*Enterobacter cloacae*) (FERM-P No. 1893) was inoculated as a seed in a seed medium composed of meat extract (1.0%), peptone (1.0%), yeast extract (0.3%), table salt (0.3%) and sorbitol (2.0%). The pH of the seed medium was adjusted to 7.3 before sterilization, and the medium cultured at a temperature of 30° C for 24 hours with shaking. The resultant seed was put into a 2-liter Florence flask containing a fermentation medium having the following composition.

| sucrose | 10.0% | yeast extract | 0.1% |
|---|---|---|---|
| ammonium sulphate | 1.0% | KCl | 0.8% |
| M$_g$SO$_4$ | 0.1% | K$_2$HPO$_4$ | 0.02% |
| F$_e$SO$_4$ | 40 mg/l | ZnSO$_4$ | 3 mg/l |

The pH of the fermentation medium was adjusted to 7.0 before sterilization and the cultivation was carried out at 30° C for 24 hours using a rotary shaking method to yield 205 mg of 2'-APG per liter of the fermented liquor which was then centrifuged to obtain the supernatent solution. The supernatent (3 liters) was passed through a resin column packed with Amberlite IRC-50 (tradename for a weakly acidic ion exchange resin in H-form, available from Rohm & Haas, U.S.A.) and eluted with 0.5N aqueous ammonia. It was then passed through a resin column packed with Diaion SK 1B (tradename for a strongly acidic ion exchange resin in NH$_4$-form, available from Mitsubishi Kasei Kogyo Kabushiki Kaisha, Japan) and eluted with 10mM aqueous ammonia. After concentration, the solution was made up with 10mM aqueous ammonia and was passed through a column packed with Diaion HP (tradename for a synthetic absorbing agent, available from Mitsubishi Kasei Kogyo Kabushiki Kaisha, Japan). The eluted fraction containing 2'-APG were collected, concentrated and then acetone added (10 times the quantity of the fractions). The supernatent was concentrated to obtain crystals of 2'-APG (440 mg) having a melting point of 252°–254° C (decomp.).

EXAMPLE 2

The cultivation was carried out in an analogous manner to that described in Example 1 with the exception that sodium inosinate (0.5 g/l) was added to the fermentation medium. There were obtained 660 mg of 2'-APG per liter of the fermented liquor.

EXAMPLE 3

The seed culture was prepared in an analogous manner to that described in Example 1 with the exception that the seed was cultured for 15 hours and then transferred to a 30-liter jar fermentor containing 18 liters of the fermentation medium having the same composition as that described in Example 1. The ratio of inoculation was 5% based upon the quantity of the fermentation medium. During the fermentation which was carried out at a temperature of 30° C for 24 hours with shaking (350 r.p.m.) and aeration (one liter of sterilized air per 1 liter of the medium), the pH of the medium was controlled to 6.5 to 7.0 with aqueous ammonia. After completion of the cultivation, the fermented liquor contained 300 mg/l of 2'-APG. By treating the fermented liquor in an analogous manner to that described in Example 1, there were obtained crystals of 2'-APG (2.9g).

EXAMPLE 4

The cultivation was carried out in an analogous manner to that described in Example 3 with the exception that xanthylic acid (sodium salt) was added to the fermentation medium to give a concentration of 1 g/l. After completion of the fermentation there was obtained 800 mg of 2'-APG per liter of the fermented liquor which was then treated in an analogous manner to that described in Example 1 to give 92 g of crystals of 2'-APG.

Having described in the present invention, that which is sought to be protected is set forth in the following claims.

We claim:

1. A process for producing (2'-amino-2'-deoxypentofuranosyl) guanine, comprising culturing a microorganism capable of producing (2'-amino-2'-deoxypentofuranosyl) guanine and belonging to the genus Aerobacter in a culture medium, and recovering the accumulated (2'-amino-2'-deoxypentofuranosyl) guanine from the fermented liquor.

2. The process of claim 1 wherein the microorganism is one belonging to the species of *Aerobacter cloacae*.

3. The process of claim 2 wherein the microorganism is Aerobacter cloacae (FERM-P No. 1893).

4. The process of claim 1 wherein culturing is effected at a temperature of from 20° to 40° C and at a pH of 5 to 8.

5. The process of claim 4 wherein the culture medium contains a carbon source, a nitrogen source and inorganic compounds.

6. The process of claim 4 where a pH of 6 to 7 is employed during cultivation.

7. The process of claim 1 wherein after cultivation, the fermented liquid is centrifuged and the supernatant liquid passed through a series of ion exchange resin column with intermittent elution thereof with aqueous ammonia in order to obtain a fraction rich in the desired product.

8. The process of claim 7 wherein said fraction is treated with acetone and the supernatant liquid concentrated to give crystals of (2'-amino-2'-deoxypentofuranosyl) guanine.

* * * * *